US008889912B2

(12) United States Patent
Allgeier et al.

(10) Patent No.: US 8,889,912 B2
(45) Date of Patent: Nov. 18, 2014

(54) PROCESS FOR PREPARING 1,6-HEXANEDIOL

(71) Applicant: E I du Pont de Nemours and Company, Wilmington, DE (US)

(72) Inventors: Alan Martin Allgeier, Wilmington, DE (US); David Richard Corbin, West Chester, PA (US); Wathudura Indika Namal De Silva, Rahway, NJ (US); Ekaterini Korovessi, Wilmington, DE (US); Carl Andrew Menning, Newark, DE (US); Joachim C Ritter, Wilmington, DE (US); Sourav Kumar Sengupta, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/870,099

(22) Filed: Apr. 25, 2013

(65) Prior Publication Data

US 2013/0231505 A1    Sep. 5, 2013

Related U.S. Application Data

(63) Continuation-in-part of application No. 13/729,494, filed on Dec. 28, 2012.

(60) Provisional application No. 61/639,449, filed on Apr. 27, 2012, provisional application No. 61/639,436, filed on Apr. 27, 2012, provisional application No. 61/639,404, filed on Apr. 27, 2012, provisional application No. 61/582,067, filed on Dec. 30, 2011.

(51) Int. Cl.
 *C07C 209/16* (2006.01)
 *C07C 29/132* (2006.01)
 *C07D 309/10* (2006.01)
 *C07D 307/12* (2006.01)

(52) U.S. Cl.
 CPC ............. *C07C 209/16* (2013.01); *C07C 29/132* (2013.01); *C07D 309/10* (2013.01); *C07D 307/12* (2013.01)
 USPC ........................................................ 564/480

(58) Field of Classification Search
 CPC .................................................... C07C 209/16
 See application file for complete search history.

(56) References Cited

U.S. PATENT DOCUMENTS

| | | | |
|---|---|---|---|
| 2,082,025 A | 6/1937 | Peters | |
| 2,201,347 A | 5/1940 | Rittmeister | |
| 2,440,929 A | 5/1948 | Frederick | |
| 2,768,213 A | 10/1956 | Whetstone et al. | |
| 3,070,633 A | 12/1962 | Utne et al. | |
| 3,083,236 A | 3/1963 | Utne et al. | |
| 3,189,651 A | 6/1965 | Ellery et al. | |
| 3,215,742 A | 11/1965 | Horlenko et al. | |
| 3,223,714 A | 12/1965 | Manly et al. | |
| 3,268,588 A | 8/1966 | Horlenko et al. | |
| 3,270,059 A | 8/1966 | Winderl et al. | |
| 3,917,707 A | 11/1975 | Williams et al. | |
| 3,933,930 A | 1/1976 | Dougherty et al. | |
| 4,254,059 A | 3/1981 | Grey et al. | |
| 4,400,468 A | 8/1983 | Faber | |
| 4,401,823 A | 8/1983 | Arena | |
| 4,780,552 A | 10/1988 | Wambach et al. | |
| 5,112,994 A | 5/1992 | Koseki et al. | |
| 5,210,335 A | 5/1993 | Schuster et al. | |
| 5,412,111 A | 5/1995 | Matsumoto et al. | |
| 5,538,891 A | 7/1996 | Schneider et al. | |
| 5,696,303 A | 12/1997 | Darsow et al. | |
| 5,981,769 A | 11/1999 | Baur et al. | |
| 6,008,418 A | 12/1999 | Baur et al. | |
| 6,087,296 A | 7/2000 | Harper | |
| 6,147,208 A | 11/2000 | Achhammer et al. | |
| 6,265,602 B1 | 7/2001 | Voit et al. | |
| 6,403,845 B1 | 6/2002 | Pfeffinger et al. | |
| 6,407,294 B1 | 6/2002 | Breitscheidel et al. | |
| 6,433,192 B1 | 8/2002 | Fischer et al. | |
| 6,462,220 B1 | 10/2002 | Luyken et al. | |
| 6,593,481 B1 | 7/2003 | Manzer | |
| 6,818,781 B2 | 11/2004 | Bhatia | |
| 7,019,155 B2 | 3/2006 | Manzer | |
| 7,230,145 B2 | 6/2007 | Kadowaki et al. | |

(Continued)

FOREIGN PATENT DOCUMENTS

| | | |
|---|---|---|
| CA | 2800797 A1 | 12/2011 |
| CN | 101628875 A | 1/2010 |
| CN | 102190639 A | 9/2011 |
| DE | 4238493 C1 | 4/1994 |
| EP | 110089 B1 | 1/1988 |
| EP | 0411403 A1 | 2/1991 |
| EP | 0418925 A2 | 3/1991 |
| EP | 1243573 A1 | 9/2002 |
| EP | 1243673 A1 | 9/2002 |

(Continued)

OTHER PUBLICATIONS

International Search Report dated Mar. 29, 2013, PCT/US2012/062314.

(Continued)

*Primary Examiner* — Brian J Davis

(57) ABSTRACT

Disclosed are processes for preparing 1,6-hexanediol from levoglucosenone. In one embodiment, the process comprises contacting levoglucosenone with hydrogen in the presence of a hydrogenation catalyst comprising palladium, platinum/tungsten, nickel/tungsten, rhodium/rhenium, or mixtures thereof at a first temperature between about 50° C. and 100° C. and at a first reaction pressure between about 50 psi and 2000 psi for a first reaction period, and at a second temperature between about 120° C. and 250° C. and at a second pressure between about 500 psi and 2000 psi for a second reaction period to form a product mixture comprising 1,6-hexanediol, wherein the first reaction period is the amount of time in which the levoglucosenone has a conversion of at least about 95%. In one embodiment, the 1,6-hexanediol is converted to 1,6-diaminohexane.

12 Claims, No Drawings

(56) References Cited

U.S. PATENT DOCUMENTS

| | | | |
|---|---|---|---|
| 8,053,608 | B2 | 11/2011 | Kouno et al. |
| 8,053,615 | B2 | 11/2011 | Cortright et al. |
| 8,501,989 | B2 | 8/2013 | Boussie et al. |
| 8,524,925 | B2 | 9/2013 | Sabesan et al. |
| 8,669,393 | B2 | 3/2014 | Boussie et al. |
| 2003/0212298 | A1 | 11/2003 | Brasse et al. |
| 2006/0014988 | A1 | 1/2006 | Fischer et al. |
| 2007/0287845 | A1 | 12/2007 | Lilga et al. |
| 2008/0200698 | A1 | 8/2008 | Reichert et al. |
| 2009/0156841 | A1 | 6/2009 | Sanborn et al. |
| 2009/0314992 | A1 | 12/2009 | Pinkos et al. |
| 2010/0113841 | A1 | 5/2010 | Suzuki et al. |
| 2010/0216958 | A1 | 8/2010 | Peters et al. |
| 2010/0274030 | A1 | 10/2010 | Bevinakatti et al. |
| 2010/0317822 | A1 | 12/2010 | Boussie et al. |
| 2011/0040131 | A1 | 2/2011 | Kouno et al. |
| 2011/0071306 | A1 | 3/2011 | Robinson |
| 2011/0218318 | A1 | 9/2011 | Boussie et al. |
| 2011/0263916 | A1 | 10/2011 | Bao et al. |
| 2011/0312051 | A1 | 12/2011 | Kalnes et al. |
| 2012/0010419 | A1 | 1/2012 | Pinkos et al. |
| 2012/0022298 | A1 | 1/2012 | Pinkos et al. |
| 2012/0035399 | A1 | 2/2012 | Abillard et al. |
| 2012/0059174 | A1 | 3/2012 | Abillard et al. |
| 2012/0116122 | A1 | 5/2012 | Feist et al. |
| 2012/0172579 | A1 | 7/2012 | Qiao et al. |
| 2013/0172578 | A1 | 7/2013 | Allgeier et al. |
| 2013/0172579 | A1 | 7/2013 | Desilva et al. |
| 2013/0172580 | A1 | 7/2013 | Ritter et al. |
| 2013/0172586 | A1 | 7/2013 | Desilva et al. |
| 2013/0172629 | A1 | 7/2013 | Allgeier et al. |
| 2013/0184495 | A1 | 7/2013 | Dias et al. |
| 2013/0289311 | A1 | 10/2013 | Allgeier et al. |
| 2013/0289312 | A1 | 10/2013 | Allgeier et al. |
| 2013/0289318 | A1 | 10/2013 | Allgeier et al. |
| 2013/0289319 | A1 | 10/2013 | Allgeier et al. |
| 2014/0228596 | A1 | 8/2014 | Allgeier et al. |

FOREIGN PATENT DOCUMENTS

| | | |
|---|---|---|
| EP | 2390247 A1 | 11/2011 |
| JP | 04041449 A | 2/1992 |
| JP | 04046133 A | 2/1992 |
| JP | 2003183200 A | 7/2003 |
| JP | 2006036653 A | 2/2006 |
| JP | 04555475 B2 | 9/2010 |
| KR | 100645668 B1 | 11/2006 |
| KR | 100688765 B1 | 2/2007 |
| WO | 9955654 A1 | 11/1999 |
| WO | 20071035896 A2 | 9/2004 |
| WO | 2007103596 A3 | 9/2007 |
| WO | 2009126852 A1 | 10/2009 |
| WO | 2009133787 A1 | 11/2009 |
| WO | 2010333789 A2 | 3/2010 |
| WO | 20100033789 A3 | 3/2010 |
| WO | 2010062689 A2 | 6/2010 |
| WO | 2010099201 A1 | 9/2010 |
| WO | 2010115759 A2 | 10/2010 |
| WO | 2010115759 A3 | 10/2010 |
| WO | 2010144873 A1 | 12/2010 |
| WO | 2011149339 A1 | 12/2011 |
| WO | 2013027766 A1 | 2/2013 |
| WO | 2013066776 A1 | 5/2013 |
| WO | 2013109477 A1 | 7/2013 |

OTHER PUBLICATIONS

International Search Report dated Apr. 29, 2013, PCT/US2012/071891.
international Search Report dated Apr. 29, 2013, PCTUS2012/071907.
International Search Report dated Apr. 29, 2013, PCT/US2012/071893.
International Search Report dated Apr. 29, 2013, PCT/US2012/071912.
International Search Report dated Apr. 30, 2013, PCT/US2012/071894.
International Search Report dated Jul. 26, 2013, PCT/US2013/038403.
International Search Report dated Jul. 18, 2013, PCT/US2013/038418.
International Search Report dated Jul. 24, 2013, PCT/US2013/038441.
International Search Report dated Jul. 24, 2013, PCT/US2013/038436.
Office actions dated Jun. 26, 2013 and Sep. 13, 2013 for copending U.S. Appl. No. 13/729,390.
Office actions dated Sep. 27, 2013 and Dec. 17, 2013 for copending U.S. Appl. No. 13/729,464.
Notice of allowance dated Oct. 1, 2013 for copending U.S. Appl. No. 13/729,494.
Notice of allowance dated Nov. 19, 2013 for copending U.S. Appl. No. 13/729,401.
Office actions dated Dec. 20, 2013 for copending U.S. Appl. No. 13/729,507.
Co-pending application, U.S. Appl. No. 14/031,356, filed Sep. 19, 2013.
Co-pending application, U.S. Appl. No. 61/782,172, filed Mar. 14, 2013.
Co-pending application, U.S. Appl. No. 61/782,198, filed Mar. 14, 2013.
Notice of allowance dated Jan. 13, 2014 for copending U.S. Appl. No. 13/729,494.
Abe, R. et al, "Photocatalytic overall water splitting under visible light by TaON and WO3 with an IO3-/I-shuttle redox mediator", Chem Commun, 2005, 3829-3831.
Adkins, H. et al, "The catalytic hydrogenation of organic compounds over copper chromite", J Am Chem Soc (1931), vol. 53, 1093.
Alexeev, O.S. et al, "gamma-Al2O3-Supported Pt catalysts with extremely high dispersions resulting from Pt-W interactions", J Catal , 190 (2000) 157-17.
Binder et al., "Simple chemical transformation of lignocellulosic biomass into furans for fuels and chemicals", J Am Chem Soc (2009) 131, 1979-1985.
Blanc, B. et al, "Starch-derived polyols for polymer technologies: preparation by hydrogenolysis on metal catalysts", Green Chemistry, Apr. 2000, 89-91.
Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.
Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-6190.
Caes et al., "Conversion of Fructose into 5-(Hydroxymethyl)furfural in Sulfolane", ChemSusChem, (2011), 4(3), 353-356.
Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.
Chen, K. et al, "C—O bond hydrogenolysis of cyclic ethers with OH groups over rhenium-modified supported iridium catalysts", J Catalysis (2012) vol. 294, 171-183.
Chia, M. et al, "Selective hydrogenolysis of polyols and cyclic ethers over bifunctional surface sites on rhodium-rhenium catalysts", J Am Chem Soc (2011) vol. 133, No. 32, 12675-12680.
Connor, R. et al, "Hydrogenolysis of Oxygenated Organic Compounds", J Am Chem Soc (1932), vol. 54, 4678-4690.
Corma, a. "Inorganic Solid Acids and Their Use in Acid-Catalyzed Hydrocarbon Reactions", (1995) Chem. Rev., 95, 559-614.
Diebold, U. "The surface science of titanium dioxide", Surface Science Reports 48 (2003) 53-229.
Efremov, A.A., "Transformations of levoglucosenone at the anhydroglucoside bond", Chem Natural Compounds (1998) 34, 5, 582-589.
Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.

(56) References Cited

OTHER PUBLICATIONS

French, G.J. et al, "A re-investigation of the thermal decomposition of ammonium paratungstate", J. Mat. Sci, 16 (1981) 3427-3436.

Gong, L. et al, "Selective hydrogenolysis of glycerol to 1,3-propanediol over a Pt/WO3/TiO2/SiO2 catalyst in aqueous media", Appl Catal A General 390 (2010) 119-126.

Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.

Helberger et al, Justus Liebigs Annalen der Chemie (1949) 561, 215-220.

Huang, L. et al, "Direct conversion of glycerol into 1,3-propanediol over Cu-H4SiW12O40/SiO2 in vapor phase", Catal Lett, 131 (2009) 312-320.

Jae, J. et al, "Investigation into the shape selectivity of zeolite catalysts for biomass conversion", Journal of Catalysis (2011) 279, 257-268.

Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.

Jayaraman, S. et al, "Synthesis and Characterization of Pt-WO3 as Methanol Oxidation Catalysts for Fuel Cells", J Phys Chem B, 2005, 109, 22958-22966.

Jung, M.E. et al, "Synthesis of Methylene-Expanded 2',3'-Dideoxyribonucleosides", J Organic Chemistry 63 (1998) 8133-8144.

Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.

Karinen, R. et al, "Biorefining: heterogeneously catalyzed reactions of carbohydrates for the production of furfural and hydroxymethyfurfural", Chem Sus Chem (2011) 4, 1002-1016.

Kaufmann, W.E. et al, "The use of platinum oxide as a catalyst in the reduction of organic compounds. IV. Reduction of furfural and its derivatives", J Am Chem Soc (1923) 45, 3029-3044.

Kiss, A.B. et al, "Thermal polycondensation of ammonium paratungstate, (NH4)10[W12O40(OH)2].4H2O", J. Materials Sci, 13 (1978) 2541-2547.

Koso, S. et al, "Chemoselective hydrogenolysis of tetrahydrofurfuryl alcohol to 1,5-pentanediol", Chem. Commun. (2009) 2035-2037.

Koso, S. et al, "Promoting effect of Mo on the hydrogenolysis of tetrahydrofurfuryl alcohol to 1,5-pentanediol over Rh/SiO2", J Catalysis 267 (2009), 89-92.

Kuba, S. et al, "Structure and properties of tungstated zirconia catalysts for alkane conversion", J Catalysis, 216 (2003) 353-361.

Lee, U. et al, "Structure of pentasodium trihydrogenhexatungstoplatinate(IV) icosahydrate", Acta Cryst. (1983) C39, 817-819.

Li, N.; Huber, G.W., "Aqueous-phase hydrodeoxygenation of sorbitol with Pt/SiO2-Al2O3: identification of reaction intermediates", Journal of Catalysis (2010) 270, 48-59.

Li, N. et al, "Renewable gasoline from aqueous phase hydrodeoxygenation of aqueous sugar solutions prepared by hydrolysis of maple wood", Green Chemistry 2011, 13, 91-101.

Liu, L. et al, "Mesoporous WO3 supported Pt catalyst for hydrogenolysis of glycerol to 1,3-propanediol", Chin. J Catal., 2012, 33, 1257-1261.

Miftakhov, M.S. et al, "Levoglucosenone: the properties, reactions, and use in fine organic synthesis", Russian Chem Reviews (1994) 63(10) 869-882.

Nakagawa, Y. et al, "Heterogeneous catalysis of the glycerol hydrogenolysis", Catal Sci Technol 2011, 1, 179-190.

Nakagawa, Y. et al., "Production of 1,5-pentanediol from biomass via furfural and tetrahydrofurfuryl alcohol", Catalysis Today 195 (2012) 136-143.

Nikolla, E. et al., "'One-Pot' Synthesis of 5-(Hydroxymethyl)furfural from Carbohydrates Using Tin-Beta Zeolite", ACS Catal. (2011), 1, 408-410.

Okuhara, T. et al, "Insoluble heteropoly compounds as highly active catalysts for liquid-phase reactions", J. Mol. Catal. 74 (1992) 247-256.

Ott, L. et al, "Catalytic Dehydration of Glycerol in sub- and supercritical water: a new chemical process for acrolein production", Green Chemistry, 2006, pp. 214-220, vol. 8.

Pae, Y.I. et al, "Characterization of NiO-TiO2 modified with WO3 and catalytic activity for acid catalysis", Bull. Korean Chem. Soc. 2004, vol. 25(12), 1881-1888.

Ponder, G. R. et al, "Pyrolytic Conversion of Biomass of Anhydrosugars—Influences of Indigenous Ions and Polysaccharide Structures", Applied Biochem Biotech, 1990, vol. 24/25, p. 41-47.

Roman-Leshkov, Y. et al., "Solvent effects on fructose dehydration to 5-hydroxymethylfurfural in biphasic systems saturated with inorganic salts", Top Catl. (2009) 52:297-303.

Shafizadeh, F. et al., "Some Reactions of Levoglucosenone", Carbohydrate Research, 1979, pp. 169-191, vol. 71.

SRI Process Economics Program, 31, Hexamethylenediamine Nov. 1967.

Ten Dam, J. et al, "Pt/Al2O3 catalyzed 1,3-propanediol formation from glycerol using tungsten additives", ChemCatChem (2013), 5(2), 497-505.

Tong, X. et al, "Biomass into chemicals: conversion of sugars to furan derivatives by catalytic processes", Appl. Catalysis a General, 385 (2010) 1-13.

Tripathy, P.K. et al, "A comparative study on the thermal decomposition of ammonium p-tungstate in batch and fluidized-bed reactors", Ind Eng Chem Res 36 (1997) 3602-3606.

Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC.

Xu, W. et al, "Direct catalytic conversion of furfural to 1,5-pentanediol by hydrogenolysis of the furan ring under mild conditions over Pt/Co2AlO4 catalyst" Chem Comm, Royal Society of Chemistry (2011) vol. 47, No. 13, 3924-3926.

Yamazoe, S. et al, "XAFS Study of Tungsten L1-, L3- Edges: Structural Analysis of Loaded Tungsten Oxide Species", Envir Sci, Research Frontiers 2008, Spring 8, 138-139.

Yamazoe, S. et al, "XAFS Study of Tungsten L1- and L3-Edges: Structural Analysis of WO3 Species Loaded on TiO2 as a Catalyst for Photo-oxidation of NH3", J. Phys Chem C 2008, 112, 6869-6879.

Yoshinaga, Y. et al, "Shape-selective oxidation catalysed by a Pt-promoted ultramicroporous heteropoly compound", J.Chem. Soc. Faraday Trans 1998, 94(15) 2235-2240.

Zanardi, M.M. et al, "Synthesis of a simple chiral auxiliary derived from levoglucosenone and its application in a Diels-Alder reaction", Tetrahedron letters 50 (2009) 999-1002.

Alamillo, R. et al., "Selective Hydrogenation of Biomass-Derived 5-Hydroxymethylfurfural Using Heterogeneous Catalysts", Green Chem., 2012, 14, 1413.

Jung, K.J. et al., "Furfural Decarbonylation Catalyzed by Charcoal Supported Palladium: Part I—Kinetics", Biomass 16 (1988) 63-76.

Jung, K.J. et al., "Furfural Decarbonylation Catalyzed by Charcoal Supported Palladium: Part II—A Continuous Process", Biomass 16 (1988) 89-96.

Lichtenthaler, F.W. "Carbohydrates as Organic Raw Materials" 2010 Wiley-VCH Verlag GmbH&Co. KGaA, Weinheim 10.1002/14356007.n05_n07.

Qin, L.-Z. et al., "Aqueous-phase deoxygenation of glycerol to 1,3-propanediol over Pt/WO3/ZrO2 catalysts in a fixed-bed reactor", Green Chem., 2010, 12, 1466-1472.

Rao, R.S. et al., "Furfural Hydrogenation Over Carbon-Supported Copper", Catalysis Letters 60 (1999) 51-57.

Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.

International Search Report dated May 6, 2014, PCT/US2012/062314.

Copending application No. PCT/US14/23874 filed Mar. 12, 2014.
Copending application No. PCT/US14/23905 filed Mar. 12, 2014.
Notice of allowance dated Mar. 11, 2014 for copending U.S. Appl. No. 13/870,091.

(56) References Cited

OTHER PUBLICATIONS

Notice of allowance dated Mar. 26, 2014 for copending U.S. Appl. No. 13/870,072.
Office action dated Apr. 9, 2014 for copending U.S. Appl. No. 13/870080.
Notice of allowance dated Apr. 25, 2014 for copending U.S. Appl. No. 13/729,464.
Notice of allowance dated Apr. 28, 2014 for copending U.S. Appl. No. 13/729,494.
Notice of allowance dated Apr. 29, 2014 for copending U.S. Appl. No. 13/729,507.
Office action dated May 7, 2014 for copending U.S. Appl. No. 13/729,390.
Database CAPLUS on STN, AN 1979:151575, Nishino et al, JP 53149905 A, Dec. 27, 1978 (abstract).
Database WPIX on STN, AN 1979-11181B, Nishino et al, JP53149905 A Dec. 27, 1978 (abstract).
Notice of allowance dated Jun. 10, 2014 for copending U.S. Appl. No. 13/870,091.
Notice of allowance dated Jun. 23, 2014 for copending U.S. Appl. No. 13/870,072.
Co-pending application published as US-2013-0172579-A1, filed Dec. 28, 2012.
Co-pending application published as 2013-0172586-A1, filed Dec. 28, 2012.
Co-pending application published as US-2013-0172580-A1, filed Dec. 28, 2012.
Co-pending application published as US-2013-0172629-A1, filed Dec. 28, 2012.
Co-pending application published as US-2013-0289318-A1, filed Apr. 25, 2013.
Co-pending application published as US-2013-0289312-A1, filed Apr. 25, 2013.
Co-pending application published as US-2013-0289319-A1, filed Apr. 25, 2013.
Co-pending application, published as US-2013-0289311-A1, filed Apr. 25, 2013.
Co-pending application published as US-2013-0172578-A1, filed Dec. 28, 2012.
Co-pending application, U.S. Appl. No. 13/870,095, filed Apr. 25, 2013
Co-pending application, U.S. Appl. No. 13/870,095, filed Apr. 25, 2013.
Efremov, A.A. et al, "Conversions of Levoglucosenone in Acid Media", Sibirskii Khimicheskii Zhurnal, 1992, 6, 34-39 Translation.
office action dated Feb. 27, 2014 for copending U.S. Appl. No. 13/870,095.

PROCESS FOR PREPARING 1,6-HEXANEDIOL

This application is a Continuation-In-Part of application Ser. No. 13/729,494 filed Dec. 28, 2012.

FIELD OF DISCLOSURE

The present invention relates to processes for preparing 1,6-hexanediol, and to processes for converting it to 1,6-diaminohexane.

BACKGROUND

Industrial chemicals obtained from inexpensive sources are desirable for use in industrial processes, for example as raw materials, solvents, or starting materials. It has become increasingly desirable to obtain industrial chemicals or their precursors from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Biomass sources for such materials are becoming more attractive economically versus petroleum-based ones. Although the convergent and selective synthesis of $C_5$ and $C_6$ carbocyclic intermediates from biomass is difficult because of the high degree of oxygenation of many components of biomass, use of such biomass-derived intermediates as feedstocks would offer new routes to industrially useful chemicals.

1,6-Hexanediol is a useful intermediate in the industrial preparation of nylon. For example, 1,6-hexandiol can be converted by known methods to 1,6-hexamethylene diamine, a useful monomer in nylon production.

There is an existing need for processes to produce 1,6-hexanediol, and synthetic intermediates useful in the production of 1,6-hexanediol, from renewable biosources. There is an existing need for processes to produce 1,6-hexanediol, as well as synthetic intermediates useful in the production of 1,6-hexanediol, from biomass-derived starting materials, including $C_6$ oxygenated hydrocarbons such as levoglucosenone. There is also an existing need to produce 1,6-hexanediol from biomass-derived starting materials and to convert it to useful products such as 1,6-diaminohexane.

SUMMARY

Disclosed herein are processes for converting levoglucosenone to 1,6-hexanediol. In one embodiment, a process is disclosed, the process comprising: contacting levoglucosenone with hydrogen in the presence of a hydrogenation catalyst comprising palladium, platinum/tungsten, nickel/tungsten, rhodium/rhenium, or mixtures thereof at a first temperature between about 50° C. and 100° C. and at a first reaction pressure between about 50 psi and 2000 psi for a first reaction period, and at a second temperature between about 120° C. and 250° C. and at a second reaction pressure between about 500 psi and 2000 psi for a second reaction period to form a final product mixture comprising 1,6-hexanediol, wherein the first reaction period is the amount of time in which the levoglucosenone has a conversion of at least about 95%.

In another embodiment of the process, the final product mixture further comprises 1,2,5,6-tetrahydroxyhexane or 2-hydroxymethyl-5-hydroxytetrahydropyran, or both.

In some embodiments, the process comprises:

(a) contacting levoglucosenone with hydrogen in the presence of a hydrogenation catalyst comprising palladium, platinum/tungsten, nickel/tungsten, rhodium/rhenium, or mixtures thereof at a first temperature between about 50° C. and 100° C. and at a first reaction pressure between about 50 psi and 2000 psi for a first reaction period, wherein the first reaction period is the amount of time in which the levoglucosenone has a conversion of at least about 95%; and at a second temperature between about 120° C. and 250° C. and at a second reaction pressure between about 500 psi and 2000 psi for a second reaction period to form a final product mixture comprising 1,6-hexanediol;

(b) isolating the 1,6-hexanediol from the final product mixture;

(c) contacting the 1,6-hexanediol with ammonia and hydrogen in the presence of a reductive amination catalyst at a temperature and for a time sufficient to form an amination product mixture comprising 1,6-diaminohexane; and (d) optionally, isolating the 1,6-diaminohexane from the amination product mixture.

DETAILED DESCRIPTION

As used herein, where the indefinite article "a" or "an" is used with respect to a statement or description of the presence of a step in a process disclosed herein, unless the statement or description explicitly provides to the contrary, the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "biomass" refers to any hemicellulosic or lignocellulosic material and includes materials comprising hemicellulose, and optionally further comprising cellulose, lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

Hemicellulose is a non-cellulosic polysaccharide found in lignocellulosic biomass. Hemicellulose is a branched heteropolymer consisting of different sugar monomers. It typically comprises from 500 to 3000 sugar monomeric units.

Lignin is a complex high molecular weight polymer and can comprise guaiacyl units as in softwood lignin, or a mixture of guaiacyl and syringyl units as in hardwood lignin.

As used herein, the abbreviations "Lgone" and "LGone" refer to levoglucosenone, also known as 1,6-anhydro-3,4-dideoxy-p-D-pyranosen-2-one. The chemical structure of levoglucosenone is represented by Formula (I).

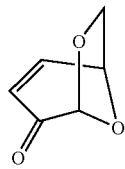

I

As used herein, the abbreviations "Lgol" and "LGol" refer to levoglucosanol, also known as 1,6-anhydro-3,4-dideoxyhexopyranose, and include a mixture of the threo and erythro stereoisomers. The chemical structure of 1,6-anhydro-3,4-dideoxyhexopyranose is represented by Formula (II).

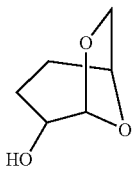

II

As used herein, the abbreviation "K128" refers to 1,6-anhydro-3,4-dideoxy-p-D-pyranose-2-one. The chemical structure of 1,6-anhydro-3,4-dideoxy-p-D-pyranose-2-one is represented by Formula (III).

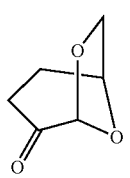

III

As used herein, the abbreviation "Tetraol" refers to 1,2,5,6-tetrahydroxyhexane, also known as 3,4-dideoxyhexitol,
and includes a mixture of stereoisomers. The chemical structure of 1,2,5,6-tetrahydroxyhexane is represented by Formula (IV).

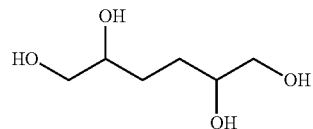

IV

As used herein, the abbreviation "THFDM" refers to tetrahydro-2,5-furandimethanol, also known as 2,5-bis[hydroxymethyl]tetrahydrofuran, and includes a mixture of stereoisomers (cis- and racemic trans-isomers). The chemical structure of tetrahydro-2,5-furandimethanol is represented by Formula (V).

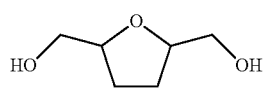

V

As used herein, the abbreviation "1,2,6-HT" refers to 1,2,6-hexanetriol and includes a racemic mixture of isomers. The chemical structure of 1,2,6-hexanetriol is represented by Formula (VI).

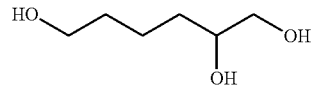

VI

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (VII).

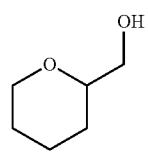

VII

As used herein, the abbreviation "HOTHPM" refers to 2-hydroxymethyl-5-hydroxytetrahydro-2H-pyran, also known as 1,5-anhydro-3,4-dideoxyhexitol, and includes a mixture of stereoisomers. The chemical structure of 2-hydroxymethyl-5-hydroxytetrahydro-2H-pyran is represented by Formula (VIII).

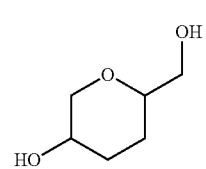

VIII

As used herein, the abbreviation "1,6-HD" refers to 1,6-hexanediol. The chemical structure of 1,6-hexanediol is represented by Formula (IX).

IX

As used herein, the abbreviation "1,2-HD" refers to 1,2-hexanediol and includes a racemic mixture of isomers. The chemical structure of 1,2-hexanediol is represented by Formula (X).

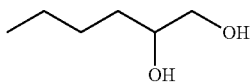

X

As used herein, the abbreviation "1,2-CHD" refers to 1,2-cyclohexanediol and includes a mixture of stereoisomers (cis and racemic trans isomers). The chemical structure of 1,2-cyclohexanediol is represented by Formula (XI).

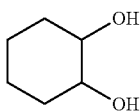

XI

As used herein, the abbreviation "1,5-HD" refers to 1,5-hexanediol and includes a racemic mixture of isomers. The chemical structure of 1,5-hexanediol is represented by Formula (XII).

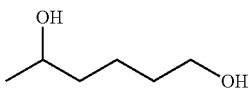

XII

As used herein, the abbreviation "HexOH" refers to 1-hexanol. The chemical structure 1-hexanol is represented by Formula (XIII).

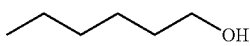

XIII

As used herein, the abbreviation "PentOH" refers to 1-pentanol. The chemical structure 1-pentanol is represented by Formula (XIV).

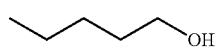

XIV

As used herein, the abbreviation "A128" refers to 1,6-anhydro-3,4-dideoxy-β-erythro-hex-3-enopyranose, also known as levoglucosenol. The chemical structure of A128 is represented by Formula (XV).

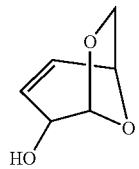

XV

Disclosed herein are processes for obtaining 1,6-hexanediol, and synthetic intermediates useful in the production of 1,6-hexanediol, from levoglucosenone, which in turn can be derived from a renewable biosource. As used herein, the term "renewable biosource" includes biomass and animal or vegetable fats or oils.

A renewable biosource can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology*, Vol 24/25, 41-41 (1990)) or Shafizadeh (*Carbohydrate Research*, 71, 169-191 (1979)). In some embodiments, levoglucosenone as obtained by pyrolysis of biomass contains small amounts of acidic components, including formic acid, acetic acid, and levulinic acid.

In the processes disclosed herein, levoglucosenone is contacted with hydrogen in the presence of a hydrogenation catalyst comprising palladium, platinum/tungsten, nickel/tungsten, rhodium/rhenium, or mixtures thereof at a first temperature between about 50° C. and about 100° C. and at a first reaction pressure between about 50 psi and 2000 psi for a first reaction period, and at a second temperature between about 120° C. and 250° C. and a second pressure between about 500 psi and 2000 psi for a second reaction period to form a final product mixture comprising 1,6-hexanediol. In some embodiments, the final product mixture further comprises 1,2,5,6-tetrahydroxyhexane or 2-hydroxymethyl-5-hydroxytetrahydropyran, or both.

For contacting with hydrogen in the presence of a hydrogenation catalyst, the levoglucosenone is typically dissolved or suspended in a liquid medium, referred to herein as a "solvent". Suitable solvents include water, a $C_1$-$C_{20}$ alcohol, a $C_2$-$C_{20}$ ether, a $C_2$-$C_{20}$ ester, or mixtures thereof. Examples of suitable alcohols which are commercially available include methanol, ethanol, propanol, butanol, and hexanol. Examples of suitable ethers which are commercially available include dibutylether, dihexylether, methyl-t-butyl-ether, tetrahydrofuran, and dioxane. Examples of suitable esters which are commercially available include ethyl acetate, butyl acetate, methyl butyrate, ethyl butyrate, butyl butyrate and hexyl acetate.

The concentration of levoglucosenone in the solvent, whether dissolved or as a suspension, is between about 1 wt % and about 50 wt %; in some embodiments it is between and optionally includes any two of the following values: 1 wt %, 5 wt %, 10 wt %, 15 wt %, 20 wt %, 25 wt %, 30 wt %, 35 wt %, 40 wt %, 45 wt %, and 50 wt %. It is anticipated that higher concentrations of levoglucosenone in water, or even neat levoglucosenone, could be used. The optimal concentration will depend on the intended reaction conditions.

The levoglucosenone, hydrogenation catalyst, and hydrogen are contacted at a first temperature between about 50° C. and about 100° C., for example between about 60° C. and about 90° C. In some embodiments, the first temperature is between and optionally includes any two of the following values: 50° C., 60° C., 70° C., 80° C., 90° C., and 100° C.

The levoglucosenone, hydrogenation catalyst, and hydrogen are contacted at a first reaction pressure between about 50 psi and 2000 psi, for example between about 200 psi and 1000 psi, or between about 500 psi and 1500 psi. In some embodiments, the first reaction pressure is between and optionally includes any two of the following values: 50, 100, 200, 300, 400, 500, 600, 700, 800, 900, 1000, 1100, 1200, 1300, 1400, 1500, 1600, 1700, 1800, 1900, and 2000 psi. In some embodiments, the first reaction pressure is between and optionally includes any two of the following values: 200, 300, 400, 500, 600, 700, 800, 900, and 1000 psi. In some embodiments, the first reaction pressure is between and optionally includes any two of the following values: 500, 600, 700, 800, 900, 1000, 1100, 1200, 1300, 1400, 1500, 1600, 1700, 1800, 1900, and 2000 psi. Optionally, an inert gas can be used in combination with the hydrogen, with the proviso that the amount of any inert gas should be such that it has no negative impact on the formation of the final product mixture.

The levoglucosenone, hydrogenation catalyst, and hydrogen are contacted at a first temperature and at a first reaction pressure for a first reaction period. The first reaction period is defined as the amount of time in which the levoglucosenone has a conversion of at least about 95%, that is, the amount of time sufficient to react at least about 95% of the sum of levoglucosenone and any 1,6-anhydro-3,4-dideoxy-p-D-pyranose-2-one isomers and/or 1,6-anhydro-3,4-dideoxy-β-erythro-hex-3-enopyranose isomers to one or more chemical species, including levoglucosanol. The amount of time corresponding to the first reaction period is determined by the specific reaction conditions selected, that is, the particular catalyst and its amount relative to the levoglucosenone, the first and second temperatures, and the first and second pressures employed.

As the levoglucosenone is contacted with the hydrogenation catalyst and hydrogen at a first temperature and a first reaction pressure, an intermediate reaction mixture is formed. The intermediate reaction mixture comprises levoglucosenone reaction products, many of which are intermediates in the production of 1,6-hexanediol. The intermediate reaction mixture comprises one or more of levoglucosanol, 1,2,5,6-tetrahydroxyhexane, 2-hydroxymethyl-5-hydroxytetrahydropyran, tetrahydrofuran-2,5-dimethanol, 1,2,6-hexanetriol, and 2-hydroxymethyltetrahydropyran. The intermediate reaction mixture also comprises any unreacted levoglucosenone. In the processes disclosed herein, levoglucosanol may be produced and converted as a mixture of stereoisomers (threo- and erythro isomer); tetrahydrofuran-2,5-dimethanol may be produced and converted as a mixture of stereoisomers (cis- and trans isomer with respect to the hydroxymethy groups attached to the tetrahydrofuran ring: one cis meso compound a trans racemate); 2-hydroxymethyltetrahydropyran may be produced and converted as a racemate; 1,2,5,6-tetrahydroxyhexane may be produced and converted as a mixture of stereoisomers differing only in the configuration of the C2 and C5 carbon atom (one meso compound and a racemate); 1,2,6-hexanetriol may be produced and converted as racemate; and 2-hydroxymethyl-5-hydroxytetrahydropyran may be produced and converted as a mixture of stereoisomers (two racemic stereoisomers).

When the first reaction period ends, that is, the levoglucosenone has reached a conversion of at least about 95%, the intermediate reaction mixture is contacted with hydrogen in the presence of the hydrogenation catalyst at a second temperature and at a second reaction pressure for a second reaction period to form a final product mixture comprising 1,6-hexanediol.

The second temperature is between about 120° C. and about 250° C., for example between about 120° C. and about 180° C., or for example between about 150° C. and about 230° C. In some embodiments, the second temperature is between and optionally includes any two of the following values: 120° C., 130° C., 140° C., 150° C., 160° C., 170° C., 180° C., 190° C., 200° C., 210° C., 220° C., 230° C., 240° C., and 250° C. In some embodiments, the second temperature is between and optionally includes any two of the following values: 120° C., 130° C., 140° C., 150° C., 160° C., 170° C., and 180° C. In some embodiments, the second temperature is between and optionally includes any two of the following values: 150° C., 160° C., 170° C., 180° C., 190° C., 200° C., 210° C., 220° C., and 230° C.

The second reaction pressure is between about 500 psi and 2000 psi, for example between about 500 psi and 1000 psi, or between about 500 psi and 1500 psi. In some embodiments, the second reaction pressure is between and optionally includes any two of the following values: 500, 600, 700, 800, 900, 1000, 1100, 1200, 1300, 1400, 1500, 1600, 1700, 1800, 1900, and 2000 psi. In some embodiments, the second reaction pressure is between and optionally includes any two of the following values: 500, 600, 700, 800, 900, and 1000 psi. In some embodiments, the second reaction pressure is between and optionally includes any two of the following values: 500, 600, 700, 800, 900, 1000, 1100, 1200, 1300, 1400, and 1500 psi.

The second reaction period is the amount of time sufficient for formation of the final product mixture comprising 1,6-hexanediol. Higher yield of 1,6-hexanediol may be obtained with a longer second reaction period, as more of the intermediates are converted to 1,6-hexanediol. In some embodiments, the final reaction product mixture further comprises 1,2,5,6-tetrahydroxyhexane or 2-hydroxymethyl-5-hydroxytetrahydropyran, or both. In one embodiment, the final product mixture comprises 1,6-hexanediol. In one embodiment, the final product mixture comprises 1,6-hexanediol and 2-hydroxymethyl-5-hydroxytetrahydropyran. In one embodiment, the final product mixture comprises 1,6-hexanediol, 2-hydroxymethyl-5-hydroxytetrahydropyran, and 1,2,5,6-tetrahydroxyhexane. In one embodiment, the final product mixture comprises 1,6-hexanediol and 1,2,5,6-tetrahydroxyhexane.

At the end of the second reaction period, if desired, the hydrogenation catalyst can be separated from the final product mixture by methods known in the art, for example by filtration. After separation from the catalyst, if desired the product mixture components, including one or more of 1,6-hexanediol, 2-hydroxymethyl-5-hydroxytetrahydropyran, and 1,2,5,6-tetrahydroxyhexane, can be separated from one another using any appropriate method known in the art, for example distillation.

The processes disclosed herein can be run in batch or continuous modes, in liquid phase, gas phase, or biphasic conditions. In a batch or continuous mode of operation, the amount of the hydrogenation catalyst used will depend on the specific equipment configuration and reaction conditions.

Hydrogenation catalysts suitable for use in the disclosed processes are those which are able to convert levoglucosenone in the presence of hydrogen to a final product mixture comprising 1,6-hexanediol under the disclosed reaction conditions. Suitable hydrogenation catalysts are those which can effect conversion of at least about 95% of the sum of levoglucosenone and any 1,6-anhydro-3,4-dideoxy-p-D-pyranose-2-one isomers and/or 1,6-anhydro-3,4-dideoxy-β-erythro-hex-3-enopyranose isomers to one or more chemical species, including levoglucosanol, at a first reaction temperature between about 50° C. and 100° C. and at a first reaction pressure between about 50 psi and 2000 psi, and then form a product mixture comprising 1,6-hexanediol at a second temperature between about 120° C. and 250° C. and at a second reaction pressure between about 500 psi and 2000 psi.

In some embodiments, the hydrogenation catalyst comprises palladium, platinum/tungsten, nickel/tungsten, rhodium/rhenium, or mixtures thereof. Examples of suitable palladium catalysts include palladium supported on carbon. Examples of suitable nickel/tungsten catalysts include Ni/W/$TiO_2$ and Ni/W/Zeolite HY, which may be prepared as described for Pt/W/$TiO_2$ in Example 1 using $Ni(NO_3)_2$ as a reagent. In one embodiment, the hydrogenation catalyst comprises platinum/tungsten or rhodium/rhenium, optionally on a solid support. In one embodiment, the hydrogenation catalyst comprises platinum/tungsten supported on $TiO_2$, and the molar ratio of platinum to tungsten is in the range of 10:1 to 1:10. In one embodiment, the hydrogenation catalyst comprises rhodium/rhenium supported on silica, and the molar ratio of rhodium to rhenium is in the range of 10:1 to 1:10.

In some embodiments, the hydrogenation catalyst comprises a metal M1 and a metal M2 or an oxide of M2, and optionally a solid support, wherein:

M1 is Pd, Pt, or Ir; and M2 is Mo, W, V, Mn, Re, Zr, Ni, Cu, Zn, Cr, Ge, Sn, Ti, Au, or Co; or M1 is Rh and M2 is Re, Mo, W, V, Mn, Ni, Cu, Zn, Cr, Ge, Sn, Ti, Au, or Zr; or M1 is Ag, Au or Co; and M2 is Re, Mo, or W;

M1 is Cu, Pd, Fe, or Ni; and M2 is Re, Mo, Cu, Zn, Cr, Ge, Sn, or W; or

M1 is Ag, Pt, Cu, or Au, and M2 is Ni, Fe, Sn, Ge, or Ir; or

M1 is Co and M2 is Fe; or

M1 is N1 and M2 is Co or Fe; or

M1 is Mn and M2 is Cr.

The M1 and M2 components of the catalysts may be derived from any appropriate metal compound. Examples include but are not limited to: rhodium (III) chloride hydrate, copper (II) nitrate hydrate, nickel (II) chloride hexahydrate, iridium (IV) chloride hydrate, iron (III) nitrate nonahydrate, tetraammineplatinum (II) nitrate, platinum chloride, hexachloroplatinic acid, tetrachloroplatinic acid, palladium chloride, palladium nitrate, palladium acetate, iridium trichloride, ammonium perrhenate, ammonium tungsten oxide hydrate, ammonium molybdate hydrate, manganese (II) nitrate hydrate, and ammonium vanadium oxide.

The loading of M1 may be 0.1-50% but preferably 0.5-5% by weight, based on the weight of the prepared catalyst (i.e., including the solid catalyst support where present). The loading of M2 may be 0.1-99.9%, preferably 2-10%. Preferably the atomic ratio of M1 to M2 in catalysts containing both M1 and M2 is 1:0.5 to 1:5. Optionally, M2 may be incorporated into the catalyst support or serve as the catalyst support, e.g. Pt supported on tungsten oxide or molybdenum oxide. Regarding the catalyst, all percentages are interpreted as weight percent relative to the weight of the prepared catalyst.

In some embodiments, the hydrogenation catalyst comprises metals M1, M2, and M3 and optionally a support, wherein M1 is Mn, Cr, V, or Ti; M2 is Ni, Co, or Fe; and M3 is Cu, Ag, Pt, Pd or Au; or M1 is Pt or Rh; M2 is Cu, Ni or Pd; and M3 is Mo, Re or W.

In some embodiments, it is useful to utilize a solid catalyst support to enhance the stability and economic feasibility of the process. Examples of supports include, without limitation: $WO_3$, $SiO_2$, $Al_2O_3$, carbon, $TiO_2$, $ZrO_2$, $CeO_2$, $SiO_2$—$Al_2O_3$, clays (e.g., montmorillonite), $SiO_2$—$TiO_2$, tungstated $ZrO_2$, aluminosilicates and zeolites (such as H—Y zeolite), $V_2O_5$, and $MoO_3$. In other embodiments, it may be desirable to not have a solid support.

The prepared hydrogenation catalyst can be in any physical form typical for heterogeneous catalysts, including but not limited to: powdered (also known as "fluidized") forms with 0.01-150 μm particle size, formed tablets, extrudates, spheres, engineered particles having uniform 0.5-10 mm size, monolithic structures on which surfaces the catalyst is applied, or combinations of two or more of the above. When a solid support is utilized a catalyst containing both M1 and M2, it is desirable that M1 be intimately associated with the M2 component, the M3 component, or both, as measured by transmission electron microscopy with energy dispersive spectroscopy. It is further preferable that the particle size of the M1 component be less than 10 nm and most preferably less than 3 nm as measured by the same techniques. In this case, particle size of the M1 component may be interpreted as particle size of a mixture of the M1 and M2 components, an alloy of the M1 and M2 components, a particle of the M1 component adjacent to a particle of the M2 component, or a particle of the M1 component on the support which contains the M2 component.

The hydrogenation catalysts can be synthesized by any conventional method for preparing catalysts, for example, deposition of metal salts from aqueous or organic solvent solutions via impregnation or incipient wetness, precipitation of an M1 component and/or an M2 component and/or an M3 component, or solid state synthesis. Preparation may comprise drying catalyst materials under elevated temperatures from 30-250° C., preferably 50-150° C.; calcination by heating in the presence of air at temperatures from 250-800° C., preferably 300-450° C.; and reduction in the presence of hydrogen at 100-400° C., preferably 200-300° C., or reduction with alternative reducing agents such as hydrazine, formic acid or ammonium formate. The above techniques may be utilized with powdered or formed particulate catalyst materials prepared by tableting, extrusion or other techniques common for catalyst synthesis. Where powdered catalysts materials are utilized, it will be appreciated that the catalyst support or the resulting catalyst material may be sieved to a desired particle size and that the particle size may be optimized to enhance catalyst performance.

The processes disclosed herein are advantageous in that only one catalyst is needed for the conversion of levoglucosenone to 1,6-hexanediol, thus avoiding any need to separate catalyst from intermediate products or reaction mixtures. Additionally, the processes disclosed herein provide routes to 1,6-hexanediol starting from levoglucosenone, which can be derived from biomass.

The 1,6-hexanediol obtained by the processes disclosed herein can be converted to 1,6-diaminohexane, an industrially useful material. For example, 1,6-hexanediol can be reductively aminated to 1,6-hexanediamine (1,6-diaminohexane) by methods known in the art. See, for example, U.S. Pat. No. 3,215,742; U.S. Pat. No. 3,268,588; and U.S. Pat. No. 3,270,059.

In some embodiments, the processes disclosed herein further comprise the steps:

(b) isolating the 1,6-hexanediol from the final product mixture;

(c) contacting the 1,6-hexanediol with ammonia and hydrogen in the presence of a reductive amination catalyst at a temperature and for a time sufficient to form an amination product mixture comprising 1,6-diaminohexane; and (d) optionally, isolating the 1,6-diaminohexane from the amination product mixture.

The reductive amination catalyst contains at least one element selected from Groups IB, VIB, VIIB, and VIII of the Periodic Table, for example iron, cobalt, nickel, ruthenium, rhodium, palladium, osmium, copper, chromium, iridium, or platinum. The elements may be in the zero oxidation state or in the form of a chemical compound. The reductive amination catalyst may be supported, unsupported or Raney-type. In one embodiment, the reductive amination catalyst contains ruthenium. In one embodiment, the reductive amination catalyst contains nickel. In one embodiment, the reductive amination catalyst is Raney nickel. In one embodiment, the reductive amination catalyst is Raney copper. In one embodiment, the reductive amination catalyst is Raney cobalt.

The reductive amination step is conducted by contacting the 1,6-hexanediol, or the final product mixture comprising the 1,6-hexanediol, with ammonia and hydrogen in the presence of the catalyst for a time sufficient to form an amination product mixture comprising 1,6-diaminohexane. Useful temperatures for the reductive amination step are in the range of about 40° C. to 300° C., for example in the range of about 75° C. to 150° C. Typically pressures are in the range of about 2 MPa to 35 MPa, for example in the range of about 4 MPa to 12 MPa. The molar ratio of hydrogen to the 1,6-hexanediol is typically equal to or greater than 1:1, for example in the range of 1:1 to 100:1, or in the range of 1:1 to 50:1.

The reductive amination step is typically performed in liquid ammonia solvent. The ammonia is used in stoichiometric excess with reference to the 1,6-hexanediol. Typically, a molar ratio of 1:1 to 80:1 of ammonia to the 1,6-hexanediol can be used, for example a molar ratio in the range of 10:1 to 50:1. Optionally, an additional solvent such as water, methanol, ethanol, butanol, pentanol, hexanol, an, ester, a hydrocarbon, tetrahydrofuran, or dioxane, can be used. The weight ratio of the additional solvent to the 1,6-hexanediol is typically in the range of 0.1:1 to 5:1.

The reductive amination step can be performed in a fixed bed reactor or in a slurry reactor, for example a batch, continuous stirred tank reactor or bubble column reactor. The 1,6-diaminohexane may be isolated from the second product mixture by any common methods known in the art, for example fractional distillation under moderate vacuum.

In some embodiments, the process comprises:

(a) contacting levoglucosenone with hydrogen in the presence of a hydrogenation catalyst comprising palladium, platinum/tungsten, nickel/tungsten, rhodium/rhenium, or mixtures thereof at a first temperature between about 50° C. and 100° C. and at a first reaction pressure between about 50 psi and 2000 psi for a first reaction period, wherein the first reaction period is the amount of time in which the levoglucosenone has a conversion of at least about 95%; and at a second temperature between about 120° C. and 250° C. and at a second reaction pressure between about 500 psi and 2000 psi for a second reaction period to form a final product mixture comprising 1,6-hexanediol;

(b) isolating the 1,6-hexanediol from the final product mixture;

(c) contacting the 1,6-hexanediol with ammonia and hydrogen in the presence of a reductive amination catalyst at a temperature and for a time sufficient to form an amination product mixture comprising 1,6-diaminohexane; and (d) optionally, isolating the 1,6-diaminohexane from the amination product mixture.

EXAMPLES

The methods disclosed herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

The following abbreviations are used in the examples: "° C." means degrees Celsius; "wt %" means weight percent; "g" means gram; "min" means minute(s); "µL" means microliter; "wt %" means weight percent; "RV(s)" means reaction vessel(s); "PSI" means pounds per square inch; "mg/g" means milligram per gram; "µm" means micrometer; "mL" means milliliter; "mm" means millimeter and "mL/min" means milliliter per minute; "MPa" means megapascal; "GC" means gas chromatography; "MS" means "mass spectrometry", "Temp" means temperature, "Ex" means Example.

All commercial reagents were used as received. All chemicals were obtained from Sigma-Aldrich (St. Louis, Mo.) unless stated otherwise. Levoglucosenone (90% purity) was obtained from TimTec LLC (Newark, Del.).) 1,6-anhydro-3,4-dideoxy-p-D-pyranose-2-one ("K128") and 1,6-anhydro-3,4-dideoxy-β-erythro-hex-3-enopyranose ("A128") were prepared as described in Journal of Organic Chemistry, 63 (1998) 8133-8144.

Reactor feeds and reaction products were analyzed by gas chromatography using standard GC and GC/MS equipment: Agilent 5975C, HP5890, Stabilwax Column Restek Company Bellefonte, Pa. (30 m×025 mm 0.5 micron film thickness). Chemical components of reaction product mixtures were identified by matching their retention times and mass spectra to those of authentic samples.

Synthesis of Pt/W/TiO$_2$ catalyst

The Pt/W/TiO$_2$ catalyst was synthesized using the following procedure. 0.92 Grams of Aerolyst 7708 TiO$_2$ (Evonik) that had been ground with a mortar and pestle and passed through a 0.0165" mesh sieve, then wetted with 1.0 mL of deionized water, was impregnated with 0.08 g of tetraammineplatinum (II) nitrate (Strem, Cat #78-2010) dissolved in 1.0 mL of deionized water. The resulting wet suspension was vortexed for 15 minutes and then vacuum-dried at 110° C. overnight. The resulting precipitate was wetted with 1.0 mL of deionized water, and then 0.0535 g of ammonium tungsten oxide hydrate (para analogue) (Alfa, stock #22640) which had been thoroughly dissolved in 2.0 mL of deionized water was added on to the wetted precipitate. The resulting wet suspension was vortexed for 15 minutes and then vacuum-dried at 110° C. overnight. After reaching room temperature, the material was transferred to a ceramic boat and calcined in air at 400° C. for three hours. The calcined Pt/W/TiO$_2$ catalyst had a Pt loading of 4 wt % based on the total weight of the catalyst, and a 1:1 molar ratio of Pt:W.

Synthesis of Rh/Re/SiO$_2$ Catalyst

The Rh/Re/SiO$_2$ catalyst was synthesized using the following procedure. 1.795 Grams of SiO$_2$ (EMD, Cat. #9385-3) that had been ground with a mortar and pestle and passed through a 0.0165" mesh sieve, then wetted with 2.0 mL of deionized water, was impregnated with 0.204 g of rhodium (III) chloride hydrate (Strem, Cat #45-1880) dissolved in 2.0 mL of deionized water. The resulting wet suspension was vortexed for 15 minutes and then vacuum-dried at 110° C. overnight. The resulting precipitate was wetted with 2.0 mL of deionized water, and then 0.094 g of ammonium perhenate (Aldrich, stock #316954) which had been thoroughly dissolved in 2.0 mL of deionized water was added on to the wetted precipitate. The resulting wet suspension was vortexed for 15 minutes and then vacuum-dried at 110° C. for overnight. After reaching room temperature, the material was transferred to a ceramic boat and calcined in air at 400° C. for three hours. The calcined Rh/Re/SiO$_2$ catalyst had a Rh loading of 4 wt % based on the total weight of the catalyst, and a 1:0.5 molar ratio of Rh:Re.

Synthesis of Rh/Re/CBV78 Catalyst

Rh/Re/CBV780 was prepared following above procedure using the acidic zeolite "Zeolyst CBV780" (Zeolyst, CBV780, SiO$_2$/Al$_2$O$_3$ molar ratio: 80) as the support. The calcined Rh/Re/CBV780 catalyst had a Rh loading of 4 wt % based on the total weight of the catalyst, and a 1:0.5 molar ratio of Rh:Re.

Example 1

Into a glass vial equipped with a magnetic stir bar were added 37.5 mg of levoglucosenone (~90% pure), 0.75 mL of water, and about 50 mg of the Pt/W/TiO$_2$ catalyst. The vial was capped with a perforated septum to limit vapor transfer rates and placed in a stainless steel (SS316) parallel pressure reactor having 8 individual wells. Empty positions were filled with water. The reactor was connected to a high pressure gas manifold and the content was purged with nitrogen gas (1000 psi) three times before H$_2$ was added. About 800 psi of H$_2$ was added and the reactor was heated to the first temperature, 60° C. After 2 h the first temperature was increased to the second temperature, 180° C., over the course of 30 min. After 4 h at 180° C. the reactor was allowed to cool to room temperature within 2 h and depressurized. The reaction solution was diluted with n-propanol and a known amount of diethylene glycol diethyl ether as an internal standard, filtered through a standard 5 micron disposable filter and analyzed by GC and GC/MS. Analysis of the reactor effluent is given in Table 1.

As can be seen from Table 1, the yield to 1,6-hexanediol was 62%. The final product mixture also comprised 2-hydroxymethyl-5-hydroxytetrahydropyran.

TABLE 1

Product Yields for Example 1

|  | LGol | THFDM | HOTHPM | THPM | 1,6HD | 1,2,6HT | 12HD | HexOH |
|---|---|---|---|---|---|---|---|---|
| m [mg] | 3.9 | 0.4 | 0.6 | 2.6 | 20.8 | 2.1 | 1.0 | 3.2 |
| n [mmol] | 0.030 | 0.003 | 0.005 | 0.022 | 0.176 | 0.015 | 0.009 | 0.031 |
| Yield | 10% | 1% | 2% | 8% | 62% | 5% | 3% | 11% |

Examples 2-4

Examples 2, 3 and 4 were each performed according to the procedure described below and demonstrate the conversion of levoglucosenone to a final product mixture comprising 1,6-hexanediol. The catalysts, first temperatures, and second temperatures used are summarized in Table 2.

Into a 1.5 mL glass vial (ROBO Autosampler Vial available from VWR International, Radnor, Pa.) equipped with a magnetic stir bar were added 37.5 mg of levoglucosenone, 0.75 mL water, and about 20 mg of catalyst. The vial was capped with a perforated septum to limit vapor transfer rates and placed in a stainless steel (SS316) parallel pressure reactor having 8 individual wells. Any empty positions were filled with water. The reactor was connected to a high pressure gas manifold and the contents were purged with nitrogen gas (1000 psi) three times. About 1000 psi of H$_2$ was then added and the reactor was heated to the first temperature (Temp 1). After two hours the temperature was increased to the second temperature (Temp 2) and the pressure was adjusted to 1100 psi. The reactor was heated for another four hours. Subsequently, the reactor was allowed to cool to room temperature within two hours, and the pressure was released. The reaction solution was diluted with n-propanol, filtered through a standard 5 micron disposable filter, and analyzed by GC and GC/MS. Product distributions are given in Table 3.

TABLE 2

Catalysts and reaction conditions for Examples 2-4

| Example | Catalyst | Temp1 | Temp2 |
|---|---|---|---|
| 2 | Rh/Re/SiO$_2$ | 60 | 125 |
| 3 | Rh/Re/CBV780 | 60 | 125 |
| 4 | Pt/W/TiO$_2$ | 60 | 160 |

TABLE 3

Product Distributions (% mol, based on GC area % corrected using relative response factors) for Examples 3 through 5.

| Ex | LGone | K128 | LGol | THFDM | HOTHPM | THPM | 1,6-HD | 1,2-CHD | 1,2,6-HT | HexOH | PentOH | Other alcohols |
|---|---|---|---|---|---|---|---|---|---|---|---|---|
| 3 | <1 | <1 | <1 | 3 | 2 | 4 | 37 | 17 | <1 | 14 | 4 | 18 |
| 4 | <1 | <1 | <1 | 30 | 6 | 12 | 18 | 1 | <1 | 1 | 1 | 30 |
| 5 | <1 | <1 | <1 | 8 | 13 | 3 | 40 | <1 | 32 | <1 | <1 | 2 |

What is claimed is:

1. A process comprising:
   (a) contacting levoglucosenone with hydrogen in the presence of a hydrogenation catalyst comprising palladium, platinum/tungsten, nickel/tungsten, rhodium/rhenium, or mixtures thereof at a first temperature between about 50° C. and 100° C. and at a first reaction pressure between about 50 psi and 2000 psi for a first reaction period, wherein the first reaction period is the amount of time in which the levoglucosenone has a conversion of at least about 95%; and at a second temperature between about 120° C. and 250° C. and at a second reaction pressure between about 500 psi and 2000 psi for a second reaction period to form a final product mixture comprising 1,6-hexanediol;
   (b) isolating the 1,6-hexanediol from the final product mixture;
   (c) contacting the 1,6-hexanediol with ammonia and hydrogen in the presence of a reductive amination catalyst at a temperature and for a time sufficient to form an amination product mixture comprising 1,6-diaminohexane; and
   (d) optionally, isolating the 1,6-diaminohexane from the amination product mixture.

2. The process of claim 1, wherein the hydrogenation catalyst further comprises a solid support selected from the group consisting of carbon, $SiO_2$, $Al_2O_3$, $SiO_2$—$Al_2O_3$, $TiO_2$, $ZrO_2$, $CeO_2$, $WO_3$, aluminosilicates and zeolites.

3. The process of claim 1, wherein the hydrogenation catalyst comprises platinum/tungsten supported on $TiO_2$.

4. The process of claim 3, wherein the molar ratio of platinum to tungsten is in the range of 10:1 to 1:10.

5. The process of claim 1, wherein the hydrogenation catalyst comprises rhodium/rhenium supported on silica.

6. The process of claim 5, wherein the molar ratio of rhodium to rhenium is in the range of 10:1 to 1:10.

7. The process of claim 1, wherein the first reaction pressure is between about 200 psi and 1000 psi.

8. The process of claim 1, wherein the reductive amination catalyst contains at least one element selected from the group consisting of iron, cobalt, nickel, ruthenium, rhodium, palladium, osmium, copper, chromium, iridium, and platinum.

9. The process of claim 1, wherein the reductive amination catalyst contains nickel.

10. The process of claim 1, wherein the reductive amination catalyst is Raney nickel.

11. The process of claim 1, wherein the reductive amination catalyst is Raney copper.

12. The process of claim 1, wherein the reductive amination catalyst is Raney cobalt.

* * * * *